(12) United States Patent
Curtis

(10) Patent No.: US 7,754,770 B2
(45) Date of Patent: Jul. 13, 2010

(54) ANTIMICROBIAL COMPOSITION

(75) Inventor: Michael A. Curtis, Glen Rock, NJ (US)

(73) Assignee: Mason Chemical Company, Arlington Heights, IL (US)

(*) Notice: Subject to any disclaimer, the term of this patent is extended or adjusted under 35 U.S.C. 154(b) by 0 days.

(21) Appl. No.: 11/426,825

(22) Filed: Jun. 27, 2006

(65) Prior Publication Data

US 2006/0292086 A1 Dec. 28, 2006

Related U.S. Application Data

(60) Provisional application No. 60/693,936, filed on Jun. 27, 2005.

(51) Int. Cl.
*A01N 33/12* (2006.01)
*A61K 31/14* (2006.01)
(52) U.S. Cl. .................................................. 514/643
(58) Field of Classification Search ................ 424/405; 514/643
See application file for complete search history.

(56) References Cited

U.S. PATENT DOCUMENTS

| | | | | |
|---|---|---|---|---|
| 5,925,681 | A * | 7/1999 | Crisanti et al. | 514/643 |
| 6,306,805 | B1 * | 10/2001 | Bratescu et al. | 510/123 |
| 2003/0008791 | A1 | 1/2003 | Chiang | |
| 2004/0058878 | A1 * | 3/2004 | Walker | 514/27 |
| 2004/0167195 | A1 * | 8/2004 | Muller | 514/400 |

OTHER PUBLICATIONS

Draize, J. H., "Dermal Toxicity", Appraisal of the Safety of Chemicals in Food, Drugs and Cosmetics—Dermal Toxicity, Association of Food and Drug Officials of the United States, Topeka, Kansas, 1959, pp. 46-59.
International Cosmetic Ingredient Dictionary and Handbook, Seventh Edition, 1997, pp. 1661-1662.

* cited by examiner

*Primary Examiner*—Alton N Pryor
(74) *Attorney, Agent, or Firm*—Foley & Lardner LLP

(57) ABSTRACT

An antimicrobial composition is provided. The antimicrobial composition has broad antimicrobial efficacy in a format convenient for no-rinse application to the skin. The composition dries quickly, leaves the skin smooth, comfortable and adequately moisturized. A method of making the antimicrobial composition, a method of sanitizing skin using the antimicrobial composition, and a foam dispenser comprising the antimicrobial composition are also provided.

18 Claims, No Drawings

ANTIMICROBIAL COMPOSITION

BACKGROUND

Illness-related microbial pathogens typically gain access to a subject's body by way of the eyes, ears, nose, and mouth and are usually transmitted to these orifices by the hands. Therefore, sanitization of the hands and other skin which may come into contact with the eyes, ears, nose, and mouth can be an effective means to prevent the transmission of microbial pathogens and, in turn, prevent illness.

Several hand sanitizers are currently marketed. For example, Purell® Instant Hand Sanitizer is a "gelled alcohol" hand sanitizer. The Purell® product uses ethyl alcohol as the active ingredient, in a formulation with a polymer thickener to allow for ease of use. Alcohol-based skin sanitizers suffer a few significant drawbacks. First, alcohol tends to dry and irritate the skin. Second, alcohol is flammable and requires special handling and storage procedures during manufacture and formulation. Finally, alcohol has no residual efficacy. Thus, although the alcohol-based sanitizers may kill pathogenic microbes on contact, after the alcohol evaporates, there is no means for control of microbial growth.

Gelled alcohol sanitizers suffer from the further drawback that the polymer thickeners trap dead skin and bacteria cells on the surface of the skin.

Quaternary ammonium compounds, such as benzalkonium chloride, possess antimicrobial activity against a wide range of microbial pathogens, including bacteria, fungi, and viruses. Quaternary ammonium compounds have advantages over alcohol-based products. First, although quaternary ammonium compounds are broadly effective antimicrobials, these compounds demonstrate relatively low toxicity to animals. Second, quaternary ammonium compounds are essentially odorless, making them easy to formulate in personal care products Finally, quaternary ammonium compounds do not degrade or corrode materials, such as steel, plastics, and rubber.

Disinfectant compositions containing the quaternary ammonium compound, benzalkonium chloride are known, however, these compositions are generally liquid or contain polymers or surfactants which result in an unpleasant feel, such as tackiness and stickiness, on the skin following application.

Thus, there is a need for a highly effective antimicrobial composition in a format convenient for no-rinse application to the skin, which dries quickly, leaves the skin smooth, comfortable, and adequately moisturized.

SUMMARY

Accordingly, a skin sanitizer is provided which provides effective antimicrobial activity, requires no rinsing, dries quickly, and does not leave a sticky feel to the skin.

One embodiment provides an antimicrobial composition comprising an antimicrobial agent, wherein the anti-microbial agent is selected from the group consisting of benzalkonium chloride and benzethonium chloride, a foaming agent, wherein the foaming agent is selected from the group consisting of dihydroxypropyl PEG-5 linoleammonium chloride, cocamidopropyl betaine, PEG-15 cocomonium chloride, and PEG-6 cocamide, a stabilizer, wherein the stabilizer is selected from the group consisting of dihydroxyethyl cocamine oxide, cocamide DEA, cocamidopropylamine oxide, cocamine oxide, lauramine oxide, and myristamine oxide, and a conditioning agent, wherein the conditioning agent is selected from the group consisting of behentrimonium chloride, cetrimonium chloride, stearalkonium chloride, and behenoyl PG-trimonium chloride, wherein the composition does not contain alcohol.

Another embodiment provides a method of sanitizing skin comprising contacting a skin surface with the antimicrobial composition.

A further embodiment provides a foaming dispenser comprising the antimicrobial composition.

It is to be understood that both the foregoing general description and the following detailed description are exemplary and explanatory only, and are not restrictive of the invention as claimed.

DETAILED DESCRIPTION

The present inventor has discovered an antimicrobial composition, the formulation of which provides effective broad spectrum antimicrobial activity, requires no rinsing, dries quickly, and does not leave a sticky feel to the skin. Moreover, this formulation provides residual antimicrobial activity, such that formulation components continue to kill microbes after the formulation is dry.

Unless otherwise specified, "a" or "an" means "one or more." As used herein, the term "pathogenic microorganism" refers to a biological microorganism that is capable of producing an undesirable effect upon a human or an animal. Examples of pathogenic microorganisms include, but are not limited to, viruses, bacteria, fungi, spores, and the like. Pathogenic microorganism includes all such biological microorganisms whether naturally occurring or engineered.

An antimicrobial composition is provided having a formulation that has effective broad spectrum antimicrobial activity, requires no rinsing, dries quickly, and leaves the skin feeling smooth, dry and adequately moisturized. The antimicrobial composition does not include alcohol. In one embodiment the composition does not include a polymer thickener or a silicone. The composition contains an antimicrobial, a foaming agent, a stabilizer, and a conditioning agent. The composition can optionally contain moisturizers.

A suitable antimicrobial agent includes benzalkonium chloride, benzethonium chloride, or a combination of these antimicrobial agents. Any appropriate concentration of antimicrobial agent can be used. In one embodiment, the concentration of antimicrobial agent is from approximately 001% to approximately 2.0% by weight In another embodiment, the concentration of antimicrobial agent is approximately 0.1 to approximately 0.13% by weight. In a further embodiment, the concentration of antimicrobial agent is 0.1%

Benzalkonium chloride exists as a mixture of N,N-dimethyl alkyl amine homologs having the following structure. The benzalkonium antimicrobial agent can have the following structure:

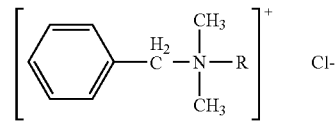

wherein R is a $C_2$-$C_{22}$ alkyl side. In one embodiment, the benzalkonium chloride is USP grade, having not less than 40% $C_{12}$, not less than 20% $C_{14}$, and not less than 70% $C_{12}$ and $C_{14}$ homologs combined. In another embodiment, the combination of $C_{12}$ and $C_{14}$ homologs is less than 90%, less than 85%, less than 80%, or less than 75% combined $C_{12}$ and $C_{14}$ homologs. In a further embodiment, the homolog distribution is approximately 67% $C_{12}$, approximately 25% $C_{14}$, approximately 7% $C_{16}$ and approximately 1% $C_{18}$.

A suitable foaming agent includes dihydroxypropyl PEG-5 linoleammonium chloride, cocamidopropyl betaine, PEG-15 cocomonium chloride, and PEG-6 cocamide, and a combination thereof. A suitable stabilizer includes dihydroxyethyl cocamine oxide, cocamide DEA, cocamidopropylamine oxide, cocamine oxide, lauramine oxide, myristamine oxide, and a combination of two or more of these foaming agents. Any appropriate concentration of foaming agent and can be used. In one embodiment, the concentration of foaming agent is from approximately 0.01% to approximately 2.0% by weight. In another embodiment, the concentration of foaming agent is approximately 0.05% to approximately 0.5% by weight. In some embodiments, the foaming agent is dihydroxyethyl cocamine oxide, and the concentration of dihydroxyethyl cocamine oxide is from approximately 0.05% to approximately 0.5%. In a further embodiment, the concentration of foaming agent is 0.3% by weight.

A suitable conditioning agent includes behentrimonium chloride, cetrimonium chloride, stearalkonium chloride, behenoyl PG-trimonium chloride, and a combination of two or more of these conditioning agents.

Any appropriate concentration of conditioning agent can be used. In one embodiment, the concentration of conditioning agent is from approximately 0.01% to approximately 2.0% by weight. In another embodiment, the concentration of conditioning agent is approximately 0.05% to approximately 0.5% by weight. In a further embodiment, the concentration of conditioning agent is 0.1%.

The composition can optionally include one or more emollients. Suitable emollients include those provided in, for example, U.S. Patent Appl. Pub. No. 2003/0008791. These emollients include, for example, acetamide MEA, agarose, ammonium lactate, arginine PCA, benzyl hyaluronate, carboxymethyl chitosan succinamide, chitosan PCA, copper PCA, corn glycerides, diglycerin, dimethyl imidazolidinone, erythritol, fructose, glucamine, glucose, glucose glutamate, glucuronic acid, glutamic acid, glycereth-7, glycereth-12, glycereth-20, glycereth-26, glycereth-31, glycerin, honey, hydrogenated honey, hydrogenated starch hydrolysate, hydrolyzed corn starch, hydrolyzed wheat starch, hydroxyethyl palmityl oxyhydroxypropyl palmitamide, hydroxyethyl sorbitol, inulin, lactamide, lactamide DEA, lactamide MEA, lactic acid, lactitol, lactose, lactulose, lysine PCA, magnesium PCA, maltitol, maltose, manganese pea, mannitol, methoxypropylgluconamide, methyl gluceth-10, methyl gluceth-20, PCA, PEG-10 propylene glycol, polyamino sugar condensate, polyglucorinic acid, polyglycerin-3, polyglycerin-4, polyglycerin-6, polyglycerin-10, potassium lactate, potassium PCA, propylene-glycol, propylene glycol citrate, saccharide hydrolysate, saccharide isomerate, sodium aspartate, sodium glucuronate, sodium hyaluronate crosspolymer, sodium lactate, sodium malate, sodium PCA, sodium polyaspartate, sorbitol, sorbityl silanediol, tea-lactate, tea-PCA, urea, xylitol, xylose, and a combination of two or more of these emollients. See also, International Cosmetic Ingredient Dictionary and Handbook, $7^{th}$ ed, pp. 1661 and 1662, which is incorporated by reference. In one embodiment the emollient is glycereth-2-cocoate. Any suitable concentration of emollients can be used. In one embodiment, the concentration of emollient is from approximately 0.01% to approximately 2.0% by weight. In another embodiment, the concentration of embodiment is approximately 0.05% to approximately 0.5% by weight. In a further embodiment, the concentration of emollient is 0.1%.

An antimicrobial composition can be supplied in its ready-to-use (RTU) concentration or as a concentrated solution. A concentrated antimicrobial composition is any antimicrobial composition that is diluted with an appropriate solvent prior to use. In one embodiment, the solvent is water.

A concentrated antimicrobial solution can from 2-times to 20-times more concentrated than the RTU solution, and, thus, prior to use the concentrated antimicrobial solution is diluted from 1:2 to 1:20 prior to use. Accordingly, in a concentrated antimicrobial solution the concentration of antimicrobial agent can be from approximately 0.02% to approximately 40% by weight, approximately 0.2% to approximately 2.6% by weight, and approximately 0.2 to approximately 2.0% by weight; the concentration of foaming agent can be from approximately 0.02% to approximately 40% by weight, approximately 0.1% to approximately 10% by weight, and approximately 0.6 to approximately 6.0% by weight; the concentration of stabilizing agent can be from approximately 0.02% to approximately 40% by weight, approximately 0.1% to approximately 10% by weight, and approximately 0.6 to approximately 6.0% by weight; the concentration of conditioning agent can be from approximately 0.02% to approximately 40% by weight, approximately 0.1% to approximately 10% by weight, and approximately 0.2 to approximately 2.0% by weight; and the concentration of emollient can be from approximately 0.02% to approximately 40% by weight, from approximately 0.1% to approximately 10% by weight, and from approximately 0.2% to approximately 2.0% by weight. For example, a 10× concentrated antimicrobial solution can have the following concentrations: 1.0% antimicrobial agent by weight, 3.0% foaming agent by weight, 1.0% conditioning agent by weight, and 1.0% emollient by weight.

In one embodiment, the antimicrobial composition can contain approximately 0.1 wt. % benzalkonium chloride, approximately 0.12 wt. % dihydroxypropyl PEG-5 linoleammonium chloride, approximately 0.1 wt. % glycereth-2 cocoate, approximately 0.9 wt. % behentrimonium chloride, approximately 0.06 wt. % dihydroxyethyl cocamine oxide, and water. In another embodiment, the antimicrobial composition can contain further contain approximately 0.05 wt. % hydroxypropyl methylcellulose, and approximately 1 wt. % butylene glycol.

The antimicrobial composition is effective against a broad spectrum of microbes, including, bacteria, virus, and fungi. In one embodiment, the antimicrobial composition can inactivate greater than 90% of a microbe, greater than 95% of a microbe, greater than 96% of a microbe, greater than 97% of a microbe, greater than 98% of a microbe, greater than 99% of a microbe, or greater than 99.9% of a microbe, within approximately 15 seconds from the time of application to an area containing microbes. In another embodiment, the antimicrobial composition can inactivate a microbe within approximately 12 seconds from the time of application, within approximately 10 seconds from the time of application, within approximately 7 seconds from the time of application, within approximately 5 seconds from the time of application, within approximately 3 seconds from the time of application, within approximately 2 seconds from the time of application, or within approximately 1 second from the time of application.

A method of sanitizing skin is also provided. The method comprises topical administration of an antimicrobial composition. Administration can be accomplished using any suitable method. In one embodiment, the antimicrobial composition is supplied as a foam and administration comprises dispensing the foam composition onto the skin, spreading the composition over the skin, and allowing the composition to dry.

An antimicrobial composition can be packaged in any suitable packaging. In one embodiment, the antimicrobial composition is packaged in a foam dispenser. In another embodiment, this dispenser is an industry standard foam dispenser. A foam dispenser containing an antimicrobial composition is also provided.

The following examples are merely exemplary and are not intended to limit the scope of the invention.

Example 1

Toxicity Studies

This example demonstrates the low toxicity and irritation exhibited by an antimicrobial composition comprising 0.1 wt. % benzalkonium chloride, 0.12 wt. % dihydroxypropyl PEG-5 linoleammonium chloride, 0.1 wt. % glycereth-2 cocoate, approximately 0.9 wt. % behentrimonium chloride, approximately 0.06 wt. % dihydroxyethyl cocamine oxide, and water (hereinafter referred to as "antimicrobial composition"). All studies discussed in this example are performed using this antimicrobial composition.

A. Eye Toxicity

The purpose of this experiment is to assess the eye irritation potiential of the antimicrobial composition when administered to the eyes.

Male New Zealand white rabbits eight to ten weeks old are used for this study. The rabbits are obtained from Kuiper Rabbitry, Gary, Ind. The rabbits weigh from 2.61 to 2.92 kilograms at the start of the study and are individually housed in stainless steel cages in a temperature, humidity, and light controlled room. Each rabbit is assigned a test animal number. The females are nulliparous and non-pregnant. The rabbits are maintained according to the recommendations contained in the National Academy Press 1996: "Guide for the Care and Use of Laboratory Animals." They are conditioned for at least five days prior to study initiation. Purina Rabbit chow and water were available ad libitum. All animals used for this study are considered to be in good health at the study initiation.

Twenty-four hours before the start of the study both eyes of the experimental animals are examined for preexisting ocular lesions. Only those animals with no preexisting ocular lesions are used for test purposes. Six animals are dosed by instilling 0.1 ml of the test composition into the conjunctival sac of one eye and then holding the eye lids together for one second to prevent loss of the material. The contralateral eye serves as the untreated control for each rabbit.

The eyes are examined at 1, 24, 48 and 72 hours after treatment. If there is no evidence of irritation at 72 hours the study is ended. Additional examinations are performed up to a maximum of 21 days, if persistent corneal involvement or other ocular irritation is present. 2% sodium fluorescein and ultraviolet light provided via a Spectroline™, Model Q-12, Long Wave UV-365 nm, 10× Magnifier, is employed to reveal possible corneal injury commencing with the 24 hour observation.

Albino rabbit and ocular route of administration used in this study in accordance with OPPTS 870.2400 Guidelines.

Group mean eye irritation scores are presented in Table 1.

TABLE 1

Group Mean Eye Irrigation Score (Draize Values)
OBSERVATION TIME - HOURS

| RABBIT NUMBER | TISSUE | 1 | 24 | 48 | 72 |
|---|---|---|---|---|---|
| 772 | Cornea (D-A) | — | 0 | 0 | 0 |
|  | Iris | 0 | 0 | 0 | 0 |
|  | Conjunctiva (R-S-D) | 4 | 8 | 2 | 0 |
|  | Total | 4 | 8 | 2 | 0 |
| 773 | Cornea (D-A) | — | 0 | 0 | 0 |
|  | Iris | 0 | 0 | 0 | 0 |
|  | Conjunctiva (R-S-D) | 2 | 2 | 0 | 0 |
|  | Total | 2 | 2 | 0 | 0 |
| 774 | Cornea (D-A) | — | 0 | 0 | 0 |
|  | Iris | 0 | 0 | 0 | 0 |
|  | Conjunctiva (R-S-D) | 4 | 0 | 0 | 0 |
|  | Total | 4 | 0 | 0 | 0 |
| 775 | Cornea (D-A) | — | 0 | 0 | 0 |
|  | Iris | 0 | 0 | 0 | 0 |
|  | Conjunctiva (R-S-D) | 4 | 0 | 0 | 0 |
|  | Total | 4 | 0 | 0 | 0 |
| 776 | Cornea (D-A) | — | 0 | 0 | 0 |
|  | Iris | 0 | 0 | 0 | 0 |
|  | Conjunctiva (R-S-D) | 4 | 2 | 0 | 0 |
|  | Total | 4 | 2 | 0 | 0 |
| 777 | Cornea (D-A) | — | 0 | 0 | 0 |
|  | Iris | 0 | 0 | 0 | 0 |
|  | Conjunctiva (R-S-D) | 2 | 0 | 0 | 0 |
|  | Total | 2 | 0 | 0 | 0 |
| Averages: |  |  |  |  |  |
|  | Cornea | — | 0 | 0 | 0 |
|  | Iris | 0 | 0 | 0 | 0 |
|  | Conjunctiva | 3.33 | 2.0 | 0.33 | 0 |
|  | Total | 3.33 | 2.0 | 0.33 | 0 |

CORNEA:
D = Density
A = Area
Corneal Score = D × A × 5
Maximum Score = 80
CONJUNCTIVA:
R = Redness
S = Swelling
D = Discharge
Conjunctival Score = (R + S + D) × 2
IRIS:
Iris Score = Value × 5
Maximum Score = 10
Sodium Fluorescein + % of corneal surface positive
Scale according to: Draize, J. H. (1965). Appraisal of the Safety of Chemicals in Foods, Drugs, and Cosmetics.

Positive eye irritation reactions in only one of the six test subjects (grade 2 erythema at the 24 hour observation) and the maximum group mean score is 3.33 at the 1 hour observation.

In accordance with the OPPTS 870.2400 Guidelines the test compound is classified as Toxicity Category III, indicating corneal involvement or irritation.

B. Oral Toxicity

The purpose of this experiment is to assess the acute toxicity of the antimicrobial composition administered orally in a single dose with a 14-day post-administration observation procedure.

Young, adult male and female Sprague-Dawley derived rats 6 to 10 weeks old and weighing between 200-221 grams are obtained from Harlan Sprague Dawley, Indianapolis, Ind. The females are nulliparous and nonpregnant. The rats are housed individually in stainless steel cages in a temperature (64-79° F.), humidity (30-70%), and light controlled room. Each animal is assigned a test animal number. The rats are maintained according to the recommendations contained in the National Academy Press 1996: "Guide for the Care and Use of Laboratory Animals." Purina Rat Chow and water are available ad libitum. The rats are acclimated at least five days prior to treatment.

One dose level of 5.0 g/kg body weight is administered orally to fasted (overnight) animals (five males/five females per dose group) according to individual body weights. Dosage volumes are administered via a metal dosing cannula. The test material is dosed neat. No mortality occurred at the 5.0 g/kg dose level during the 14 day observation period.

All test animals were observed frequently during the day of dosing and once daily for 14 days following dosing for any toxic or deleterious effects.

Table 2 provides individual observations.

TABLE 2

Oral Dosage Results

| Sex | Animal No. | HOURS | | | DAYS | | | | | | | | | | | | | |
|---|---|---|---|---|---|---|---|---|---|---|---|---|---|---|---|---|---|---|
| | | 1 | 2.5 | 4 | 1 | 2 | 3 | 4 | 5 | 6 | 7 | 8 | 9 | 10 | 11 | 12 | 13 | 14 |
| M | 21 | ✓ | ✓ | ✓ | ✓ | ✓ | ✓ | ✓ | ✓ | ✓ | ✓ | ✓ | ✓ | ✓ | ✓ | ✓ | ✓ | ✓ |
| M | 22 | ✓ | ✓ | ✓ | ✓ | ✓ | ✓ | ✓ | ✓ | ✓ | ✓ | ✓ | ✓ | ✓ | ✓ | ✓ | ✓ | ✓ |
| M | 23 | ✓ | ✓ | ✓ | ✓ | ✓ | ✓ | ✓ | ✓ | ✓ | ✓ | ✓ | ✓ | ✓ | ✓ | ✓ | ✓ | ✓ |
| M | 24 | ✓ | ✓ | ✓ | ✓ | ✓ | ✓ | ✓ | ✓ | ✓ | ✓ | ✓ | ✓ | ✓ | ✓ | ✓ | ✓ | ✓ |
| M | 25 | ✓ | ✓ | ✓ | ✓ | ✓ | ✓ | ✓ | ✓ | ✓ | ✓ | ✓ | ✓ | ✓ | ✓ | ✓ | ✓ | ✓ |
| F | 26 | ✓ | ✓ | ✓ | ✓ | ✓ | ✓ | ✓ | ✓ | ✓ | ✓ | ✓ | ✓ | ✓ | ✓ | ✓ | ✓ | ✓ |
| F | 27 | ✓ | ✓ | ✓ | ✓ | ✓ | ✓ | ✓ | ✓ | ✓ | ✓ | ✓ | ✓ | ✓ | ✓ | ✓ | ✓ | ✓ |
| F | 28 | ✓ | ✓ | ✓ | ✓ | ✓ | ✓ | ✓ | ✓ | ✓ | ✓ | ✓ | ✓ | ✓ | ✓ | ✓ | ✓ | ✓ |
| F | 29 | ✓ | ✓ | ✓ | ✓ | ✓ | ✓ | ✓ | ✓ | ✓ | ✓ | ✓ | ✓ | ✓ | ✓ | ✓ | ✓ | ✓ |
| F | 30 | ✓ | ✓ | ✓ | ✓ | ✓ | ✓ | ✓ | ✓ | ✓ | ✓ | ✓ | ✓ | ✓ | ✓ | ✓ | ✓ | ✓ |

X - Dead
✓ - Normal
A - Uncoordinated Movement
B - Lacrimation
C - Salivation
D - Loose Stool
E - Retching
F - Piloerection
G - Hypothermic to Touch
H - Hypoactive
I - Prostrate
J - Tremors
K - Labored Respiration
L - Hunched Posture
M -
O -
P -
Q -

Body weights are obtained at study initiation and at 7 and 14 days post-administration. All test animals at the end of the observation period are sacrificed by $CO_2$ asphyxiation. A complete gross necropsy is conducted on the animals.

Dosing and mortality data are presented in Table 3.

TABLE 3

Acute Oral Toxicity in Rats at 5.06 g/kg

| Rat Number | Sex | INITIAL Bwt (gm) | Dose g/kg | Dose in grams | 7 Day Bwt (gm) | 14 Day Bwt (gm) | Fate |
|---|---|---|---|---|---|---|---|
| 21 | M | 212 | 5 | 1.06 | 228 | 312 | Survived |
| 22 | M | 214 | 5 | 1.07 | 295 | 328 | Survived |
| 23 | M | 221 | 5 | 1.11 | 302 | 333 | Survived |
| 24 | M | 206 | 5 | 1.03 | 281 | 309 | Survived |
| 25 | M | 206 | 5 | 1.03 | 293 | 315 | Survived |
| 26 | F | 205 | 5 | 1.03 | 243 | 253 | Survived |
| 27 | F | 206 | 5 | 1.03 | 238 | 260 | Survived |
| 28 | F | 210 | 5 | 1.05 | 247 | 254 | Survived |
| 29 | F | 208 | 5 | 1.04 | 236 | 249 | Survived |
| 30 | F | 200 | 5 | 1.00 | 243 | 247 | Survived |

Table 4 provides the finding for the individuals in the necroscopy study.

TABLE 4

Necroscopy Findings

| RAT #/SEX | DAY | FINDINGS |
|---|---|---|
| 21/M | Final Sac | External: No gross changes observed. Internal: No gross changes observed. |
| 22/M | Final Sac | External: No gross changes observed. Internal: No gross changes observed. |
| 23/M | Final Sac | External: No gross changes observed. Internal: No gross changes observed. |
| 24/M | Final Sac | External: No gross changes observed. Internal: No gross changes observed. |
| 25/M | Final Sac | External: No gross changes observed. Internal: No gross changes observed. |

TABLE 4-continued

Necroscopy Findings

| RAT #/SEX | DAY | FINDINGS |
|---|---|---|
| 26/M | Final Sac | External: No gross changes observed. Internal: No gross changes observed. |
| 27/M | Final Sac | External: No gross changes observed. Internal: No gross changes observed. |
| 28/M | Final Sac | External: No gross changes observed. Internal: No gross changes observed. |
| 29/M | Final Sac | External: No gross changes observed. Internal: No gross changes observed. |
| 30/M | Final Sac | External: No gross changes observed. Internal: No gross changes observed. |

The administration of the test article by oral gavage at a dose of 5.0 g/kg body weight to male and female rats produced no mortality in the ten test animals. The acute oral $LD_{50}$ is determined to be greater than 5.0 g/kg body weight. Therefore, the test composition is classified as Toxicity Category IV.

C. Dermal Irritation

The purpose of this study is to assess the skin irritation potential of the composition administered by dermal application for a four hour period.

Male New Zealand white rabbits, eight to ten weeks old, are used for this study. The rabbits are obtained from Kuiper Rabbitry, Gary, Ind. The rabbits weigh from 2.66 to 2.91 kilograms at the start of the study and were individually housed in stainless steel cages in a temperature (61-72° F.), humidity (30-70%), and light controlled room. Each rabbit is assigned a test animal number. The rabbits are maintained according to the recommendations contained in the National Academy Press 1996: "Guide for the Care and Use of Laboratory Animals," and are conditioned for at least five days prior to study initiation. Purina Rabbit chow and water are available ad libitum. All animals used for this study are considered to be in good health at the study initiation.

The day before study initiation, electric clippers are used to remove the hair from the left side of the trunk, from the midline of the back to the abdomen. The following day a 0.5 ml aliquot of the test material is applied to an area approximately six square centimeters on the side of the test animal. The application site is located approximately 5-7 centimeters down from the backbone, to assure good skin contact. The composition is then covered with a 2.5 cm²-2 layer gauze patch held in place with non-irritating Kendall Curity Standard Porous Tape and the patch is covered with a semi-occlusive plastic overwrap secured in place with Kendall Curity Standard Porous Tape for the duration of the exposure period. At the end of the four-hour contact period, excess material is removed from the site and the site is observed and scored.

Dermal irritation readings for erythema and edema are performed approximately 30 minutes after patches are removed, and 4.5, 24, 48 and 72 hours after treatment. Grading and scoring of irritation are performed in accordance with the Draize scoring system (Draize, J. H. "Dermal Toxicity". Appraisal of the Safety of Chemicals in Foods, Drugs and Cosmetics—Dermal Toxicity, Assoc. of Food and Drug Officials of the U.S. Topeka, Kans., 1975 pp. 46-59). Table 5 provides scoring & individual animal observations.

TABLE 5

Observation of Intact Sites - Observation Time (Hours)

| Rabbit Number | Sex | Initial Bwt. (kg) | Final Bwt. (kg) | ER 4.5 | ED 4.5 | ER 24 | ED 24 | ER 48 | ED 48 | ER 72 | ED 72 |
|---|---|---|---|---|---|---|---|---|---|---|---|
| 794 | M | 2.66 | 2.71 | 0 | 0 | 0 | 0 | 0 | 0 | 0 | 0 |
| 795 | M | 2.75 | 2.88 | 0 | 0 | 0 | 0 | 0 | 0 | 0 | 0 |
| 796 | M | 2.50 | 2.52 | 1 | 1 | 1 | 0 | 0 | 0 | 0 | 0 |
| 797 | M | 2.73 | 2.76 | 0 | 0 | 0 | 0 | 0 | 0 | 0 | 0 |
| 798 | M | 2.78 | 2.84 | 0 | 0 | 0 | 0 | 0 | 0 | 0 | 0 |
| 799 | M | 2.91 | 2.97 | 0 | 0 | 0 | 0 | 0 | 0 | 0 | 0 |
| | | | Avg | 0.17 | 0.17 | 0.17 | 0 | 0 | 0 | 0 | 0 |
| | | | Total | 0.34 | | 0.17 | | 0 | | 0 | |

| INDEX | DESCRIPTIVE RATING |
|---|---|
| 0 | Non-irritant |
| 2 or less | Slight Irritant |
| 2-5 | Moderate Irritant |
| 5 or more | Severe Irritant |

The maximum primary skin irritation score is 0.34 at the 4.5 hour observation. The Primary Irritation Index was calculated to be 0.13. Based upon the results of this study the test material would be classified as Tox Category IV for dermal effects.

D. Dermal Toxicity

The purpose of this study is to assess the dermal toxicity potential of a antimicrobial composition administered by dermal application for a twenty-four hour contact period.

Young, adult male and female New Zealand Albino rabbits weighing between 2.18-2.54 kilograms are obtained from Kuiper Rabbitry, Gary, Ind. The females are nulliparous and nonpregnant. Rabbits are housed individually in stainless steel cages in a temperature (61-72° F.), humidity (30-70%), and light controlled room. The rabbits are maintained according to the recommendations contained in the National Academy Press 1996: "Guide for the Care and Use of Laboratory Animals." Purina Rabbit Chow and water is available ad libitum. The rabbits are acclimated at least 5 days prior to treatment. The rabbits are individually identified by an ear tag.

Initial testing with five males and five females is performed at a dose level of 2.0 g/kg. Twenty-four hours before application of the test composition, the dorsal and ventral areas of the trunks of the rabbits are shaved, the areas shaved are approximately 30% of the total body surface area. The 24-hour period between shaving and application of the material allows recovery of the stratum corneum from any disturbance caused by the shaving.

The test composition is administered neat by dermal application at a dose of 2.0 g/kg body weight to five male and five female rabbits.

All animals are weighed on the day of dosing. Based upon the animals' body weight the test material is applied uniformly over approximately 10 percent of the total body surface area, covered with two layers of porous gauze dressing and a sleeve of plastic sheeting is fitted over the shaved trunk of the animal and secured in place with non-irritating surgical tape. The test animals are returned to their cages for the 24 hour contact period. The test material remains in contact with the skin for a 24 hour period after which time the wrap is removed and any remaining material removed.

All test animals are observed frequently during the day of dosing and once daily for 14 days following dosing for any toxic or deleterious effects. All ten test animals exhibit erythema, and edema at the application site on Study Day 1. The time at which any pharmocotoxic signs appear, disappear, and their duration were recorded. No mortality occurred during the 14 day observation period. The weight of each animal was determined prior to dosing, at 7 days and at the end of the 14 days. Tables 5 and 6 provide individual animal observations.

TABLE 6

Acute Dermal Toxicity Data

| RABBIT NUMBER | SEX | INITIAL BWT (kg) | DOSE (grams) | 7 DAY BWT (kg) | 14 DAY BWT (kg) | FATE |
|---|---|---|---|---|---|---|
| 737 | F | 2.18 | 4.36 | 2.22 | 2.31 | Survived |
| 738 | F | 2.49 | 4.98 | 2.60 | 2.93 | Survived |
| 739 | F | 2.39 | 4.78 | 2.68 | 2.84 | Survived |
| 740 | F | 2.51 | 5.02 | 2.78 | 2.95 | Survived |
| 741 | F | 2.40 | 4.80 | 2.67 | 2.90 | Survived |
| 747 | M | 2.34 | 4.68 | 2.38 | 2.54 | Survived |
| 748 | M | 2.53 | 5.06 | 2.67 | 2.81 | Survived |
| 749 | M | 2.18 | 4.36 | 2.31 | 2.53 | Survived |
| 750 | M | 2.39 | 4.78 | 2.32 | 2.46 | Survived |
| 751 | M | 2.54 | 5.08 | 2.65 | 2.78 | Survived |
| 737 | F | 2.18 | 4.36 | 2.22 | 2.31 | Survived |

TABLE 7

Gross Pharmacotoxic Observations

| | | HOURS | | | DAYS | | | | | | | | | | | | | |
|---|---|---|---|---|---|---|---|---|---|---|---|---|---|---|---|---|---|---|
| Sex | Animal No. | 1 | 2 | 4 | 1 | 2 | 3 | 4 | 5 | 6 | 7 | 8 | 9 | 10 | 11 | 12 | 13 | 14 |
| F | 737 | ✓ | ✓ | ✓ | L M | L M | L | L | ✓ | ✓ | ✓ | ✓ | ✓ | ✓ | ✓ | ✓ | ✓ | ✓ |
| F | 738 | ✓ | ✓ | ✓ | L M | L | L | L | ✓ | ✓ | ✓ | ✓ | ✓ | ✓ | ✓ | ✓ | ✓ | ✓ |
| F | 739 | ✓ | ✓ | ✓ | L M | L | ✓ | ✓ | ✓ | ✓ | ✓ | ✓ | ✓ | ✓ | ✓ | ✓ | ✓ | ✓ |
| F | 740 | ✓ | ✓ | ✓ | L M | L | L | ✓ | ✓ | ✓ | ✓ | ✓ | ✓ | ✓ | ✓ | ✓ | ✓ | ✓ |
| F | 741 | ✓ | ✓ | ✓ | L M | L M | L | L | ✓ | ✓ | ✓ | ✓ | ✓ | ✓ | ✓ | ✓ | ✓ | ✓ |
| M | 747 | ✓ | ✓ | ✓ | L M | L | ✓ | ✓ | ✓ | ✓ | ✓ | ✓ | ✓ | ✓ | ✓ | ✓ | ✓ | ✓ |
| M | 748 | ✓ | ✓ | ✓ | L M | L | ✓ | ✓ | ✓ | ✓ | ✓ | ✓ | ✓ | ✓ | ✓ | ✓ | ✓ | ✓ |
| M | 749 | ✓ | ✓ | ✓ | L M | L M | L | ✓ | ✓ | ✓ | ✓ | ✓ | ✓ | ✓ | ✓ | ✓ | ✓ | ✓ |
| M | 750 | ✓ | ✓ | ✓ | L M | L | L | ✓ | ✓ | ✓ | ✓ | ✓ | ✓ | ✓ | ✓ | ✓ | ✓ | ✓ |
| M | 751 | ✓ | ✓ | ✓ | L M | L | L | L | ✓ | ✓ | ✓ | ✓ | ✓ | ✓ | ✓ | ✓ | ✓ | ✓ |

X - Dead
✓ - Normal
A - Uncoordinated Movement
B - Lacrimation
C - Salivation
D - Loose Stool
E - Retching
F - Piloerection
G - Hypothermic to touch
H - Hypoactive
I - Prostrate
J - Tremors
K - Labored Respiration
L - Erythema @ the application site
M - Edema @ the application site
N - Necrosis @ the application site
O - Coriaceousness
P - Fissuring
Q - Eschar All test animals at the end of the test period are sacrificed by an injection with Beuthanasia-D Special solution. A complete gross necropsy is conducted on the animals. No gross changes are observed for any test animal.

The administration of test sample by dermal application at a dose of 2.0 g/kg body weight to male and female rabbits produced no mortality, indicating that the dermal $LD_{50}$ of the composition is greater than 2.0 g/kg body weight.

E. Conclusions

The animal test data provided in this example, demonstrates that a antimicrobial composition containing 0.1 wt. % benzalkonium chloride, 0.12 wt. % dihydroxypropyl PEG-5 linoleammonium chloride, 0.1 wt. % glycereth-2 cocoate, approximately 0.9 wt % behentrimonium chloride, approximately 0.06 wt. % dihydroxyethyl cocamine oxide, and water exhibits extremely low toxicity and causes very little irritation, even with prolonged contact.

Example 2

Efficacy of Antimicrobial Composition

A suspension of bacterial cells is exposed to a Nobac foaming hand sanitizer composition containing the following formulation with the concentration of benzalkonium chloride as specified in the tables below.

| Ingredient | Weight % |
|---|---|
| Dihydroxypropyl PEG-5 linoleammonium chloride | 0.12 |
| Glycereth-2 cocoate | 0.10 |
| Behentrimonium chloride | 0.09 |

-continued

| Ingredient | Weight % |
|---|---|
| Dihydroxyethyl cocamine oxide | 0.06 |
| Water | 99.53 |

After exposure, an aliquot of the suspension is transferred to a neutralizing subculture media and is assayed for survivors.

TABLE 8

Nobac Foaming Hand Sanitizer with 750 ppm benzalkonium chloride

| Test Organism | Exposure Time | Test Population Control CFU/mL* | Number of Survivors CFU/mL* | $Log_{10}$ Reduction | Percent Reduction |
|---|---|---|---|---|---|
| Staphylococcus aureus | 15 seconds | $5.8 \times 10^6$ | $5.0 \times 10^2$ | 4.06 | 99.99% |
| | 30 seconds | | 6 | 6.0 | >99.9999% |
| | 45 seconds | | <2 | >6.5 | >99.9999% |
| | 60 seconds | | <2 | >6.5 | >99.9999% |

TABLE 9

Nobac Foaming Hand Sanitizer with 1000 ppm Quaternary Ammonium

| Test Organism | Exposure Time | Test Population Control CFU/mL* | Number of Survivors CFU/mL* | $Log_{10}$ Reduction | Percent Reduction |
|---|---|---|---|---|---|
| Staphylococcus aureus | 15 seconds | $5.8 \times 10^6$ | $1 \times 10^1$ | 6 | >99.999% |
| | 30 seconds | | <2 | >6.5 | >99.9999% |
| | 45 seconds | | <2 | >6.5 | >99.9999% |
| | 60 seconds | | <2 | >6.5 | >99.9999% |

TABLE 10

Nobac Foaming Hand Sanitizer with 1250 ppm benzalkonium chloride

| Test Organism | Exposure Time | Test Population Control CFU/mL* | Number of Survivors CFU/mL* | $Log_{10}$ Reduction | Percent Reduction |
|---|---|---|---|---|---|
| Staphylococcus aureus | 15 seconds | $5.8 \times 10^8$ | $3 \times 10^1$ | 5.3 | 99.999% |
| | 30 seconds | | <2 | >6.5 | >99.9999% |
| | 45 seconds | | <2 | >6.5 | >99.9999% |
| | 60 seconds | | <2 | >6.5 | >99.9999% |

*CFU = Colony Forming Unit

TABLE 11

Nobac RTU Foaming Hand Sanitizer with 1000 ppm benzalkonium chloride

| Test Organism | Exposure Time | Test Population Control CFU/mL)* | Number of Survivors (CFU/mL)* | $Log_{10}$ Reduction | Percent Reduction |
|---|---|---|---|---|---|
| Clostridium difficile | 15 seconds | $3.4 \times 10^6$ | <2 | >6.2 | >99.9999% |
| Enterococcus faecalis Vancomycin Resistant | 15 seconds | $1.12 \times 10^6$ | $3.2 \times 10^1$ | 4.54 | 99.99% |
| Escherichia coli | 15 seconds | $3.8 \times 10^6$ | 4 | 6.0 | 99.999% |
| Escherichia coli O157:H7 | 15 seconds | $1.26 \times 10^6$ | <2 | >5.8 | >99.999% |
| Klebsiella pneumoniae | 15 seconds | $1.10 \times 10^6$ | 2 | 5.7 | 99.999% |

TABLE 11-continued

Nobac RTU Foaming Hand Sanitizer with 1000 ppm benzalkonium chloride

| Test Organism | Exposure Time | Test Population Control CFU/mL* | Number of Survivors (CFU/mL)* | $Log_{10}$ Reduction | Percent Reduction |
|---|---|---|---|---|---|
| *Pseudomonas aeruginosa* | 15 seconds | $3.5 \times 10^6$ | <2 | >6.2 | >99.9999% |
| *Salmonella typhi* | 15 seconds | $1.27 \times 10^6$ | 2 | 5.8 | 99.999% |
| *Serratia marcescens* | 15 seconds | $1.81 \times 10^6$ | $7.2 \times 10^1$ | 4.40 | 99.99% |
| *Streptococcus pneumoniae* | 15 seconds | $1.43 \times 10^5$ | 2 | 4.85 | 99.99% |
| *Streptococcus pyogenes* | 15 seconds | $1.77 \times 10^6$ | <2 | >5.9 | >99.999% |

*CFU/mL = Colony Forming Units per mL of test mixture

What is claimed is:

1. An antimicrobial composition comprising:
   (a) approximately 0.1 wt. % benzalkonium chloride,
   (b) approximately 0.12 wt. % dihydroxypropyl PEG-5 linoleammonium chloride,
   (c) approximately 0.1 wt. % glycereth-2 cocoate,
   (d) approximately 0.9 wt. % behentrimonium chloride,
   (e) approximately 0.06 wt. % dihydroxyethyl cocamine oxide, and
   (f) water.

2. An antimicrobial composition comprising:
   (a) approximately 0.1 wt. % benzalkonium chloride,
   (b) approximately 0.12 wt. % dihydroxypropyl PEG-5 linoleammonium chloride,
   (c) approximately 0.1 wt. % glycereth-2 cocoate,
   (d) approximately 0.9 wt. % behentrimonium chloride,
   (e) approximately 0.06 wt. % dihydroxyethyl cocamine oxide,
   (f) approximately 0.05 wt. % hydroxypropyl methylcellulose,
   (g) approximately 1 wt. % butylenes glycol, and
   (h) water.

3. An antimicrobial composition comprising:
   (a) from approximately 0.1% to approximately 0.13% benzalkonium chloride
   (b) from approximately 0.05% to approximately 0.5% dihydroxypropyl PEG-5 linoleammonium chloride;
   (c) from approximately 0.05% to approximately 0.5% dihydroxyethyl cocamine oxide
   (d) from approximately 0.05% to approximately 0.5% glycereth-2 cocoate; and
   (e) from approximately 0.05% to approximately 0.5% behentrimonium chloride, wherein the composition does not contain alcohol.

4. A method of sanitizing skin comprising contacting a skin surface with the antimicrobial composition of claim 3.

5. A foaming dispenser comprising the antimicrobial composition of claim 3.

6. The antimicrobial composition of claim 3, comprising:
   (a) approximately 0.1% benzalkonium chloride
   (b) approximately 0.3% dihydroxypropyl PEG-5 linoleammonium chloride
   (c) approximately 0.1% dihydroxyethyl cocamine oxide
   (d) approximately 0.1% glycereth-2 cocoate, and
   (e) approximately 0.1% behentrimonium chloride.

7. The antimicrobial composition of claim 3, wherein the benzalkonium chloride is a homolog having the following formula:

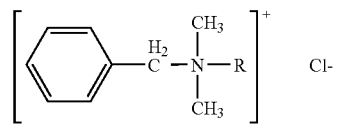

wherein R is a $C_{12}$-$C_{18}$ alkyl side chain, wherein a homolog distribution is not less than 70% $C_{12}$ and $C_{14}$ combined.

8. The antimicrobial composition of claim 6, wherein the benzalkonium chloride is a homolog having the following formula:

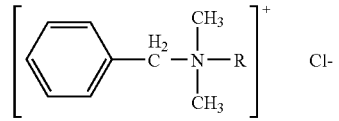

wherein R is a $C_{12}$-$C_{18}$ alkyl side chain, wherein a homolog distribution is not less than 70% $C_{12}$ and $C_{14}$ combined.

9. The antimicrobial composition of claim 3, wherein a homolog distribution is not less than 70% $C_{12}$ and $C_{14}$ combined.

10. The antimicrobial composition of claim 6, wherein a homolog distribution is not less than 70% $C_{12}$ and $C_{14}$ combined.

11. The antimicrobial composition of claim 3, wherein a homolog distribution is less than 90% combined $C_{12}$ and $C_{14}$ homologs.

12. The antimicrobial composition of claim 6, wherein a homolog distribution is less than 90% combined $C_{12}$ and $C_{14}$ homologs.

13. The antimicrobial composition of claim 3, wherein a homolog distribution is approximately 67% $C_{12}$, approximately 25% $C_{14}$, approximately 7% $C_{16}$, and 1% $C_{18}$.

14. The antimicrobial composition of claim 6, wherein a homolog distribution is approximately 67% $C_{12}$, approximately 25% $C_{14}$, approximately 7% $C_{16}$, and 1% $C_{18}$.

15. An antimicrobial composition comprising:
(a) from approximately 0.01% to approximately 2.0% of an antimicrobial agent, wherein the anti-microbial agent is selected from the group consisting of benzalkonium chloride and benzethonium chloride;
(b) from approximately 0.01% to approximately 2.0% of dihydroxypropyl PEG-5 linoleammonium chloride;
(c) from approximately 0.05% to approximately 0.5% of dihydroxyethyl cocamine oxide;
(d) from approximately 0.01% to approximately 2.0% of behentrimonium chloride; and
(e) from approximately 0.05% to approximately 0.5% glycereth-2 cocoate wherein the composition does not contain alcohol.

16. The antimicrobial composition of claim 15, comprising:
(a) from approximately 0.1% to approximately 0.13% benzalkonium chloride
(b) from approximately 0.05% to approximately 0.5% dihydroxypropyl PEG-5 linoleammonium chloride;
(c) from approximately 0.05% to approximately 0.5% dihydroxyethyl cocamine oxide
(d) from approximately 0.05% to approximately 0.5% glycereth-2 cocoate; and
(e) from approximately 0.05% to approximately 0.5% behentrimonium chloride.

17. The antimicrobial composition of claim 15, wherein the benzalkonium chloride is a homolog having the following formula:

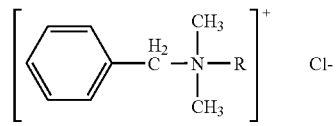

wherein R is a $C_{12}$-$C_{18}$ alkyl side chain, wherein a homolog distribution is not less than 70% $C_{12}$ and $C_{14}$ combined.

18. The antimicrobial composition of claim 15, wherein the composition inactivates greater than 99.9% of a microbe, within approximately 15 seconds from the time of application to an area containing microbes.

* * * * *